United States Patent [19]
Lee

[11] Patent Number: 4,999,885
[45] Date of Patent: Mar. 19, 1991

[54] DEVICE FOR MAINTAINING ORDERLY TUBING OR WIRING

[76] Inventor: Michael D. Lee, 3152 E. Church St., Whitehall, Pa. 18052

[21] Appl. No.: 486,794

[22] Filed: Mar. 1, 1990

[51] Int. Cl.⁵ ............................................. A44B 21/00
[52] U.S. Cl. ...................................... 24/578; 24/339; 24/575
[58] Field of Search ............ 24/578, 575, 576, 577, 24/587, 329, 331, 335, 336, 339, 615, 20 R; 128/DIG. 26; 403/59, 289, 354; 446/120, 121

[56] References Cited

U.S. PATENT DOCUMENTS

| 593,978 | 11/1897 | Boehm | 24/336 |
|---|---|---|---|
| 1,861,151 | 5/1932 | Buschman | 24/339 |
| 2,202,638 | 5/1940 | Praeg | 33/174 |
| 2,335,843 | 11/1943 | Rogoff | 403/289 |
| 2,406,895 | 4/1946 | Olson | 24/575 |
| 2,902,821 | 9/1959 | Kelly, Jr. | 59/80 |
| 3,160,175 | 12/1964 | Laemmle | 138/96 |
| 3,188,030 | 6/1965 | Fischer | 248/68 |
| 3,295,812 | 1/1967 | Schneider et al. | 24/329 |
| 3,327,360 | 6/1967 | Nichols | 24/336 |
| 3,399,322 | 8/1968 | Ambe | 403/354 |
| 3,630,195 | 12/1971 | Santomieri | 128/133 |
| 3,677,339 | 7/1972 | Perrin et al. | 165/162 |
| 3,861,015 | 1/1975 | Hooven | 29/203 |
| 3,965,540 | 6/1976 | Moore | 24/336 |
| 4,114,241 | 9/1978 | Bisping | 24/81 |
| 4,244,542 | 1/1981 | Mathews | 248/49 |
| 4,306,697 | 12/1981 | Mathews | 248/68 |
| 4,308,642 | 1/1982 | Heyman | 24/306 |
| 4,493,468 | 1/1985 | Roach | 248/62 |
| 4,579,310 | 4/1986 | Wells et al. | 248/544 |
| 4,707,906 | 11/1987 | Posey | 29/453 |
| 4,758,196 | 7/1988 | Wang | 446/120 |
| 4,795,429 | 1/1989 | Feldstein | 128/DIG. 26 |
| 4,864,697 | 9/1989 | Sparks et al. | 24/336 |

Primary Examiner—Victor N. Sakran
Attorney, Agent, or Firm—Steele, Gould & Fried

[57] ABSTRACT

A clip for orderly arrangement and identification of flexible lines such as hospital intravenous tubing has a pocket for grasping the tubing and interengaging protrusions and engagement holes whereby the clip can be chained in a line with other similar clips. The clip has a pair of arms attached at one end to a base, free ends of the arms being attachable to the base of another clip. The base has engagement holes for receiving snap-in protrusions on the free ends of the arms, the arms being spaced and the protrusions preferably protruding outwardly for insertion into engagement holes on the inside of a cavity in the base after compressing the arms together with finger pressure. Tubing or wiring which is grasped by the clips is thus maintained in neat and orderly spaced relation. The clips can be coded by color, shape or the like and are preferably placed at spaced positions along the tubes for identifying a specific tube without tracing it back to its source of destination.

25 Claims, 3 Drawing Sheets

DEVICE FOR MAINTAINING ORDERLY TUBING OR WIRING

BACKGROUND OF THE INVENTION

1. Field Of The Invention

The invention relates to the field of devices for organizing and maintaining multiple elongated members in an orderly array, especially flexible strands of tubing or wiring. The invention is chiefly intended for use with hospital intravenous tubing, but it may also be adapted for use with laboratory tubing, electrical wiring, cords, cables and the like.

2. Prior Art

A hospital patient is often connected to several different intravenous (IV) tubes, as well as drainage tubes, gas lines and the like. The tubes have various sources and various destinations around and on the patient and are not always distinguishable by their dimensions, coloration etc. Such tubing at best is disorganized due to the profusion of practically indistinguishable tubes, and can easily become entangled, leading to further confusion as to the origin and destination of particular tubes. These multiple strands of tubing, if not kept orderly, will make an unsightly mess and be a nuisance to both patient and medical personnel. Disorganized tubing is prone to catch on passing persons or equipment and can be disengaged accidentally from the patient or the source. In the event of an emergency such as a malfunction or problem at the source or destination of a particular tube, it may be important to quickly identify the tube leading thereto, and to take appropriate steps at the other end of the tube. Tubes may run some distance between an initial source, a flow control mechanism and the patient. A supply of fluid to a particular destination may have to be stopped or started, or varied in flow rate in certain instances. A medication may have to be added to a specific IV line. Some medications and IV agents are incompatible. Mistakes made under pressure can be extremely detrimental to the well being of the patient. Analogous problems can occur with respect to flexible line arrangements other than IV lines, for example electrical wiring.

Devices are known for fixing in place a point along a length of hospital tubing. Such devices typically are designed for attachment to a sheet or bedside, having a base with receptacles for tubes and a spring clip for attaching the base to the sheet or the like. The base is large enough to accommodate several tubes, being thereby unnecessarily bulky if fewer tubes are used in a particular arrangement. The base could presumably be used at an intermediate point along a tube rather than at the bed or at an attachment to the patient's garment, i.e., used to hold tubes relative to one another without using the attachment clip to fix the base in place. Nevertheless, as a practical matter these devices are only useful at the bedside or on the patient, close to the destination of the tubes. This renders the devices more limiting than helpful because tubes which otherwise could be routed out of the way must pass the base. Known tube fixing devices do not enable the tubes to be organized in a versatile manner at any point where two or more tubes come into proximity. Known devices also do not attempt to use the fixing device as a means for ready identification and tracing of individual tubes from any point along their entire length.

U.S. Pat. No. 4,308,642—Heyman discloses a tube fixing device having a base and tube receptacle as described. The Heyman device provides a pad which can be secured to a sheet or bedside by a spring loaded jaw type clip. A plurality of tubes can be secured to the pad by a piece of tape or a hook and pile (i.e., "Velcro") fastener. Heyman does not disclose a means for identifying the individual tubes. Also, the Heyman device does not allow the easy addition or removal of an individual tube without upsetting the orderly arrangement of the other tubes. Finally, the Heyman device cannot be easily repositioned along the length of the tubes, being limited as a practical matter to a bedside or patient-affixed location.

U S. Pat. No. 4,707,906—Posey discloses a tubing holder having opposed upper and lower faces forming receptacles configured to hold tubing of different sizes, and a spring loaded fastening clip for securing the holder to a sheet or bedside. However, this holder does not identify the tubes, allow easy addition or removal of tubes, or allow easy repositioning of the holder along the tubes.

There is a definite need in the health care field for an organizing device which will overcome the problems of prior art tube fixing devices, allowing a versatile but neat and out of the way arrangement of tubes, and ensuring that otherwise-indistinguishable individual tubes in any number can readily and quickly be traced between their source and destination.

SUMMARY OF THE INVENTION

It is an object of the invention to provide a device for maintaining orderly arrays of flexible lines such as hospital tubing as a means to protect the tubing from displacement and to enable quick matching of the source and destination of any particular tube.

It is another object of the invention to provide a tubing organizing device which is small, inexpensive and simple to use.

It is another object of the invention to provide a tubing organizing device which holds hospital tubing securely and along a desired path so that the tubing will not come loose unintentionally, or protrude to catch on passing items.

It is a further object of the invention to provide a tubing organizing device which is simple to remove or to reposition along the course of the tubing.

It is still another object of the invention to provide a tubing organizing device which readily identifies individual tubing lines or groups of lines in an array.

These and other objects are accomplished by a device defining a clip which slips onto a tube. Each clip comprises two arms with a space between them for the tube. The arms are attached at one end to a base. The tube is inserted between the arms and the clip is pushed onto the tube until the tube seats in a pocket in the base, dimensioned such that the tube snaps resiliently into place. Each clip has an outward facing cavity in its base into which the arms of a similar clip can be inserted such that the clips can be chained sequentially in any number. The arms have protrusions which align with engagement holes in the base of a similar clip in order to connect the clips to each other. The clips are disconnected from each other by squeezing the arms to release them from the cavity. The tubing is removed from the clip or engaged in the clip by simply sliding the clip laterally over the tube along a line defined by the arms of the clip. The clip can also be slid longitudinally along the tube, preferably subject to frictional engagement of the tube and the clip; however lateral placement is convenient and is preferred.

BRIEF DESCRIPTION OF THE DRAWINGS

There are shown in the drawings the embodiments of the invention that are presently preferred. It should be understood, however, that the invention is not limited to the precise arrangements and instrumentalities shown in the drawings, wherein.

DETAILED DESCRIPTION OF THE PREFERRED EMBODIMENTS

Figure 1:
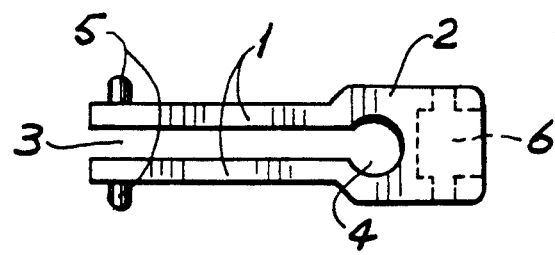
FIG. 1 is a side view of a clip according to a first embodiment of the invention.
Figure 2:
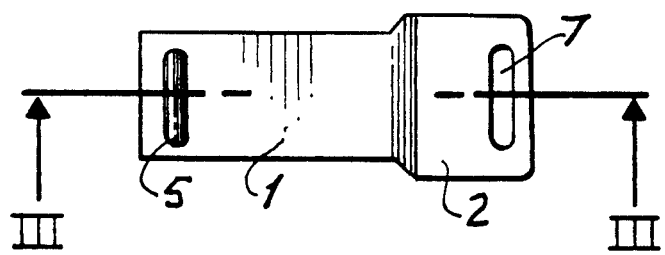
FIG. 2 is a top view of the clip according to FIG. 1.

A clip according to the invention as shown in FIG. 1 has a pair of arms 1 which are elongated in an insertion or removal direction for an elongated body such as a tube, and define a space between them for engaging the tube. In the preferred embodiment the arms are in substantially parallel alignment. The tube when inserted extends longitudinally in a direction perpendicular to the direction of elongation of the arms. The arms 1 are connected at one end to a base 2, whereby the arms are maintained with a space between them, through which a tube can be passed in the direction of elongation of the arms. The tube could also be inserted lengthwise into the space between the arms, however, it is normally undesirable to access the ends of the tubes, and instead the tube and clip preferably are attached at an intermediate point along the length of the tube.

The arms resiliently define a space 3 which can be narrowed by applying finger pressure to the arms 1 in a direction which will bring the arms closer together. The space 3 is slightly narrower than the tube's outer diameter, and the arms can splay resiliently to accommodate the tube. Typically, the tube is itself resilient and can also be compressed during insertion. Once inserted, however, the clip does not constrict the tube and therefore allows free flow of fluids in the tube.

The clip has a pocket 4 which is dimensioned to engage along the length of an elongated body such as tubing or wiring. The pocket has an internal diameter dimensioned to substantially complement the external diameter of the elongated body, e.g., tubing, wiring, etc., which is slightly wider than the space 3 between the arms. The elongated body is slidably inserted between the arms 1 of the clip, and the tubing or wiring is maneuvered through space 3 until it rests in the pocket 4. The increase in dimensions from space 3 to pocket 4 enables the tube or the like to be snapped resiliently into position, where it remains stable. Clips having pockets of various sizes and shapes can be made in order to suit the intended application, i.e., to accommodate elongated bodies of different cross sectional sizes and contours. For example, a clip for electrical AC power wiring might have a pocket with an oval cross section, to fit over the oval cross section of a wire having side by side insulated conductors.

The clips can be chained sequentially by attaching opposite ends of the clips together, forming a row of spaced tube engaging means in any length. The clips preferably are each attached to a tube or other elongated body before attachment of the clips into a chain. However, one or more of the clips in a chain can be left empty to better define divisions between groups of tubes.

Figure 3:
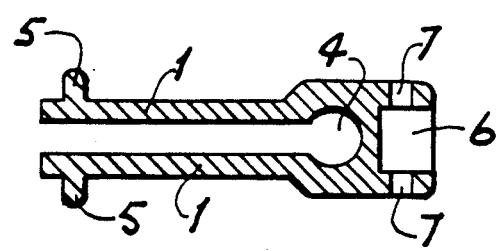
FIG. 3 is a side sectional view taken along line 3—3 of FIG. 2.

At least one protrusion 5 extends from each arm 1 at a free end thereof. At an opposite end of the clip is a cavity 6 in the base 2, as shown in FIG. 3, into which the free end of the two arms 1 can be inserted. The cavity includes engagement holes 7, dimensioned just slightly larger than the protrusions 5 in order to allow a slidable snap fit of the protrusions 5 in the engagement holes 7. The arms must be compressed from their rest position to fit within cavity 6, and upon insertion to the point of alignment of protrusions 5 with engagement holes 7, the arms snap outwardly and hold the respective clips in aligned position.

Figure 7:
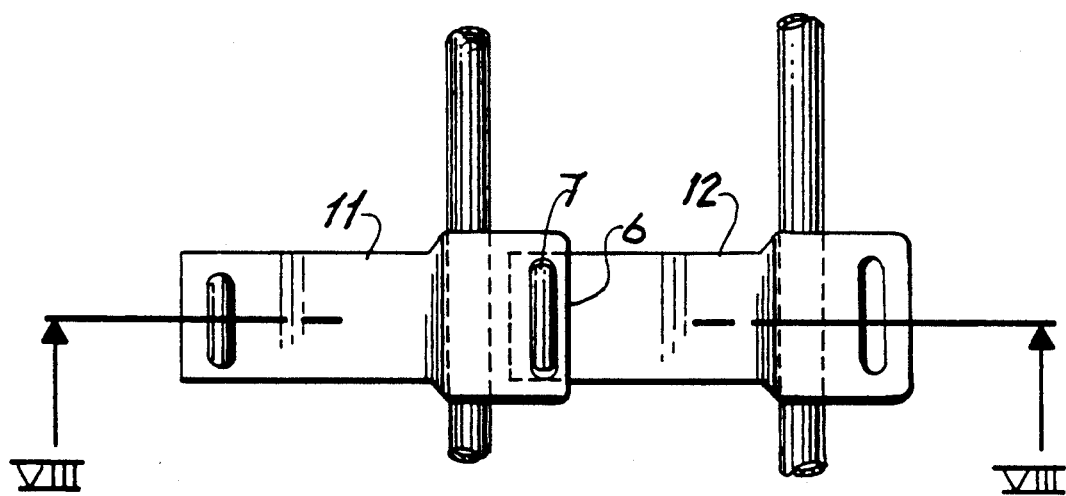
FIG. 7 top view of two clips in engagement.
Figure 8:
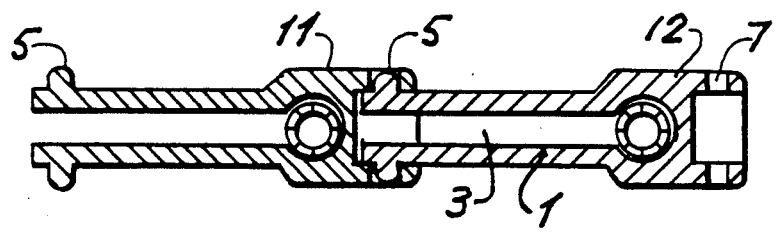
FIG. 8 is a side sectional view taken along line 8—8 of FIG. 7.

FIGS. 7 and 8 show a second clip 12 according to the invention, connected to a first clip 11 in order to hold two elongated bodies such as intravenous tubes in spaced relation. The arms 1 of the second clip 12 were first squeezed together by finger pressure, thus narrowing space 3, so that the arms 1 having protrusions 5 at their ends fit into cavity 6 of the first clip 11. Finger pressure is then released and the second clip 12 is maneuvered until protrusions 5 are aligned with engagement holes 7 in the first clip 11. As the second clip 12 and protrusions 5 align with engagement holes 7, the clips snap into secure fixed relationship to each other. Numerous additional clips according to the invention can be connected in this manner in order to organize any number of elongated bodies as desired. Clips thus joined can be easily disconnected at any of their junctions by merely squeezing together arms 1 using finger pressure until protrusions 5 are withdrawn from engagement holes 7, and then separating the clips.

Figure 4:
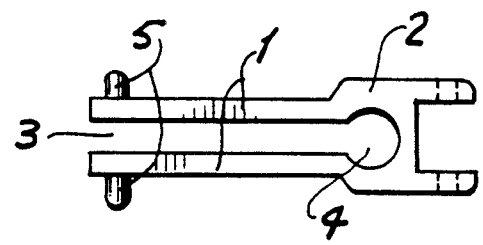
FIG. 4 is a side view of another embodiment of a clip according to the invention.
Figure 5:
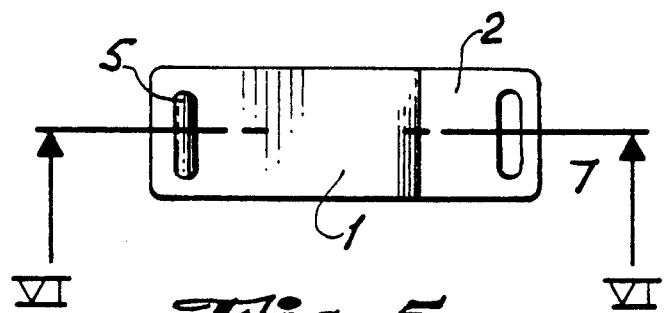
FIG. 5 top view of the embodiment shown in FIG. 4.
Figure 6:
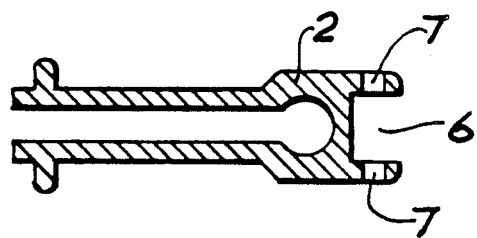
FIG. 6 is a side sectional view taken along line 6—6 of FIG. 5.

FIGS. 4, 5, and 6 show another embodiment of the clip having a narrower base such that the base 2 is no wider than the arms 1. Other shapes are also possible, and the shapes, colors or other attributes can be used to mark a particular tube or class of tubes. These classifications can be arbitrary classifications (e.g., with a unique arbitrary color or shape for each tube or other elongated body). Alternatively, it is possible to use an encoding scheme for deciding which color or shape refers to which tube content. For example, plasma products can routinely be provided with red clips, saline with blue, gas lines with green, etc. The clips can be provided with labelling means for carrying a text description of the source or destination, or perhaps including other information respecting the tube (e.g., when installed, or by whom).

Preferably, when installing a new tube in an array of tubes, the distinct shape or color of clip is employed at a plurality of positions along that tube. Therefore, in tracing a tube, the user can readily determine the particular tube in an array of tubes that corresponds to a particular source or destination, needing only to trace the tube to its first clip. If convenient, the various tubes attached to a patient can be led from the patient to a close-by centralized chain of clips for ready reference and tubes from adjacent sources can be led to a nearby chain of clips for corresponding reference at the source end.

Some forms of elongated body such as electrical wires frequently are color coded when installed. For example, in connection with domestic power wiring the hot line is black, neutral is white, ground is green and switched lines are red. Where a number of electrical wires of corresponding colors are provided, the present invention allows the wires to be grouped in accordance with their sources or destinations in addition to the coding of their type indicated by the insulation coloring. Similar coding can be used with hospital tubing, electrical wiring and flexible conduits in general. The invention is also capable of use with more rigid conduits and bodies, however, use with flexible bodies is most advantageous because the flexible bodies do not remain in alignment along their length due to initial alignment of the bodies at one end.

Figure 9:
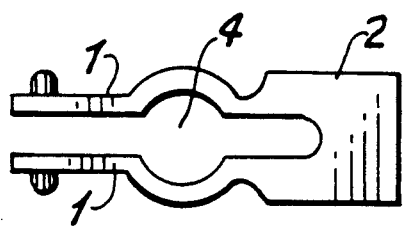
FIG. 9 is a side view of another embodiment of the clip having a pocket formed wholly by the arms of the clip.

FIG. 9 shows another embodiment of the clip wherein the pocket is centrally located along the length of the arms 1. This embodiment is better suited for grasping elongated bodies having an increased thickness because the arms are more readily expandable at a distance from their connection to the base 2. In other respects, the clip of FIG. 9 is structured and operates in the same manner as those of FIGS. 1-8.

Figure 10:
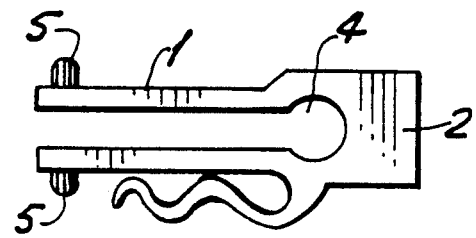
FIG. 10 is a side view of a clip having a side clip attached.

The clip of the invention can be provided with means for engaging additional items apart from other clips. FIG. 10 shows another embodiment of the clip further comprising a side clip resiliently attached to the base, and at least one further pocket formed by the side clip and dimensioned to grasp along the length of an elongated body. The side clip is particularly suited for retaining loops of excess tubing, as well as distinct elongated bodies such as for neat retracted storage of electrical cords, and the like. Moreover, this form of clip can attach a clip or an array of chained clips to fixed structures, for routing the array along a desired path.

In a typical use of the invention, the user selects a particular type of clip for designating a line to be installed in an array. The user affixes a clip according to the invention at a point preferably near to an initial point at which the line can be brought adjacent another line to be included in the array. These lines are then clipped using distinctly shaped or colored clips. The lines can extend alongside one another or can be diverted separately, however, in each case the same line is identified using a clip corresponding to the clip initially attached. If the user must remove a line from an array, its clips can be readily detached from the array and the adjacent clips can be attached such that the array remains intact. Preferably, at one or more points common to all or most of the lines, a chain of clips is included such that this point can always be examined for identifying particular lines, without tracing the lines through various routes and possibly past loops of other tubes with which they could become confused.

The clip of the invention can also be arranged such that the arms bear inwardly on the outer surfaces of the base rather than outwardly on the inner surfaces of the base, in which event the protrusions are of course directed inwardly toward space 3. In such an embodiment it is appropriate to arrange a means by which the arms can be opened with finger pressure. One example would be to arrange the arms to protrude past the base, and to shorten the base to the point that the arms could pivot resiliently on the base, in the manner of a clothespin. The arms likewise can be provided with the engagement holes and the protrusions provided on the base. In any of the embodiments, the protrusions are shaped so as to retain the attached clips in line (i.e., the protrusions are non-round in cross section or are arranged as plural pins on each arm), to thereby retain the alignment of attached clips in an orderly manner.

The invention as disclosed and claimed is a clip comprising a pair of resilient arms 1, a base 2 connected to said arms 1, preferably at one end of the arms 1, the base 2 maintaining a space 3 between the arms 1, the arms 1 being resiliently bendable remote from the base 2 for narrowing the space 3. At least one pocket 4 is defined by at least one of said arms 1 and said base 2, the pocket 4 being dimensioned to complement a section along a length of an elongated body. The base 2 has a cavity 6, said cavity 6 defining a receptacle for engaging with arms 1 of a similar said clip, whereby a plurality of said elongated bodies can be chained to position the elongated bodies in an orderly array.

At least one protrusion 5 and at least one engagement hole 7 can be disposed either on at least one of the arms 1 or on the base 2, the protrusion 5 engaging in a corresponding engagement hole 7 in the other of the arms or the base of an additional said clip for attaching the clips together. Preferably, both said arms 1 have at least one of said protrusion 5 and/or engagement hole 7, the arms 1 thereby being engageable with the base 2 of said additional clip.

At least one protrusion 5 preferably is provided on each of said arms 1, the protrusions 5 of said pair of arms 1 engaging in corresponding engagement holes 7 in said base 2. The protrusions 5 of the arms 1 preferably face outwardly and the engagement holes 7 are provided on opposed surfaces of the cavity 6 in the base 2. The cavity 6 has an internal diameter substantially corresponding to an outer dimension defined by the pair of arms 1, the arms 1 being resiliently brought together for insertion into the cavity 6 and the protrusions 5 snapping into the engagement holes 7 to chain together said clips. The pocket 4 has an internal dimension substantially equal to an outer dimension of the elongated body and the pocket 4 is preferably disposed adjacent a junction of said arms 1 and said base 2. The pocket 4 can also be located along the arms 1 at a point remote from the base 2, or located substantially within the base 2. The cavity 6 is located on a side of the base 2 opposite to a side where the arms 1 are attached, whereby the clips are chained in line. A side clip can be included, resiliently attached to at least one of said arms 1 and said base 2, for attaching the clip to an additional item. The side clip can define at least one further pocket for grasping along a length of an elongated body.

The invention more particularly is a clip for organizing flexible lines such as hospital tubing, comprising a base 2, a pair of coextensive resilient arms 1 connected to the base 2 and protruding from the base 2. At least one pocket 4 in the clip is dimensioned to receive and engage one of the flexible lines, the pocket 4 being defined by a hole through at least one of said arms 1 and said base 2, opening between the arms 1 such that the arms 1 can be passed over the flexible line laterally of the flexible line. Means 5, 6, 7 in the base 2 engage arms 1 of a similar said clip remote from a base of the similar clip, whereby a plurality of said elongated bodies can be chained to position the elongated bodies in a stable orderly array. At least one protrusion 5 on at least one of said arms 1 and/or base 2, engages in corresponding engagement holes 7 in the other of said base 2 and/or arms 1. The arms 1 are preferably spaced and the protrusions 5 extend to connect the base 2 and at least one of the arms 1 when the arms 1 are at rest, the arms 1 being resiliently movable such that the protrusion 5 can disengage, the protrusion 5 snapping resiliently into the engagement hole 7 when aligned therewith. The base 2 preferably has a cavity 6 for receiving the arms 1 of said similar clip and the protrusions 5 are provided on both the arms 1 to face outwardly and to snap into engagement holes 7 on the inside of the cavity of the base. The protrusions 5 alternatively can face inwardly to engage on depressions on the outside of the base 2.

The pocket 4 has an internal dimension substantially equal to an outer dimension of the flexible line, the internal dimension of the pocket 4 being larger than a spacing 3 between the arms 1. Preferably, the clip is distinctly identifiable over said similar clip by at least one of color, size, shape and labelling. The pocket 4 can be dimensioned to engage an intravenous line, electric cord, cable or other elongated body. The clip preferably is formed as an integral plastic body.

The invention can be characterized as a method for organizing resilient lines in an array, comprising the steps of selecting a clip for designating a line to be installed in the array, the clip having means for engaging the line and means for engaging a similar said clip such that the clips are positioned in line. The clip is affixed to the line at a point, preferably near a source, destination or an initial point along the line at which the line can be brought adjacent a second line to be included in the array. An additional clip is affixed to said second line, whereupon the clip and the additional clip are attached to one another. The clip and the additional clip are preferably distinguishable by at least one of size, shape, color and labelling.

Clips corresponding to a predetermined array of position, color, size and/or shape can be placed in successive arrays remote from a first array along a given tube. Preferably the clips are selected and affixed in order such that successive arrays have corresponding tube clips at a same relative position in each successive array to better identify the tube at any point remote from the initial point, and the resilient lines are positioned in a consistent and orderly manner.

The invention having been disclosed, a number of variations of the invention will now occur to those skilled in the art. The foregoing discussion is intended to detail exemplary embodiments of the invention rather than to limit the invention to the embodiments discussed. Reference should be made to the appended claims rather than the foregoing specification as defining the scope of exclusive right in the invention claimed.

I claim:
1. A clip comprising:
a pair of resilient arms;
a base connected to said arms, the base maintaining a space between the arms, the arms being resiliently bendable remote from the base for narrowing the space, the arms and the base being oriented in opposite directions on the clip;
at least one pocket for receiving an elongated body, the pocket being defined by at least one of said base, at least one of said arms, and said base and at least one of the arms in combination, the pocket being dimensioned to complement a section along a length of the elongated body; and,
a cavity in the base, said cavity defining a receptacle for engaging with arms of a similar said clip such that the clip and the similar clip ar attached sequentially, whereby a plurality of said clips can be chained sequentially in any number to position the elongated bodies in an orderly array.

2. The clip as defined in claim 1, wherein the pocket has an internal dimension substantially equal to an outer dimension of the elongated body and the pocket is disposed adjacent a junction of said arms and said base.

3. The clip as defined in claim 1, wherein the pocket is located along the arms at a point remote from the base.

4. The clip as defined in claim 1, wherein the pocket is located substantially within the base.

5. The clip as defined in claim 1, wherein the cavity is located on a side of the base opposite to a side where the arms are attached, whereby the clips are chained in line.

6. The clip as defined in claim 1, further comprising a side clip resiliently attached to at least one of said pair of arms and said base, for attaching the clip to an additional item.

7. The clip as defined in claim 6, wherein the side clip defines at least one further pocket for grasping along a length of an elongated body.

8. A clip comprising:
a pair of resilient arms;
a base connected to said arms, the base maintaining a space between the arms, the arms being resiliently bendable remote from the base for narrowing the space;
at least one pocket defined at least partly by one of the base and at least one of the arms, the pocket being dimensioned to complement a section along a length of an elongated body;
a cavity in the base, said cavity defining a receptacle for engaging with arms of a similar said clip, whereby a plurality of said clips can be chained to position the elongated bodies in an orderly array; and,
at least one protrusion on at least one of said arms, the protrusion engaging in a corresponding engagement hole in a second said base of an additional said clip.

9. The clip as defined in claim 8, wherein the at least one protrusion of said at least one of the arms faces outwardly relative to the arms and the engagement hole is provided on a surface of the cavity in the base.

10. The clip as defined in claim 9, wherein the cavity has an internal diameter substantially corresponding to an outer dimension defined by the pair of arms, the arms being resiliently brought together for insertion into the cavity and the protrusion snapping into the engagement hole to chain together said clips.

11. A clip comprising:
a pair of resilient arms;
a base connected to said arms, the base maintaining a space between the arms, the arms being resiliently bendable remote from the base for narrowing the space;
at least one pocket defined at least partly by one of the base and at least one of the arms, the pocket being dimensioned to complement a section along a length of an elongated body;
a cavity in the base, said cavity defining a receptacle for engaging with arms of a similar said clip, whereby a plurality of said clips can be chained to position the elongated bodies in an orderly array; and, at least one protrusion and at least one engagement hole on at least one of said pair of arms and said base, the protrusion engaging in a corresponding said engagement hole in an other of said at least one of said pair of arms and said base, said other of said at lest one of said pair of arms and said base being disposed on an additional said clip.

12. The clip as defined in claim 11, wherein both said arms have at least one of said at least one protrusion and said at least one engagement hole, the arms thereby being engageable with the base of said additional clip.

13. The clip as defined in claim 12, wherein both said arms have at least one outwardly facing protrusion, the protrusions of the arms being engageable in engagement holes provided on an inner surface of the base of the additional clip.

14. A clip for organizing flexible lines such as hospital tubing, comprising:
   a base;
   a pair of coextensive resilient arms connected to the base and protruding in one direction from the base;
   at least one pocket in the clip, dimensioned to receive and engage one of the flexible lines, the pocket being defined by a hole bounded by at least one of said base, at least one of said arms, and said base and at least one of the arms in combination, the pocket opening between the arms such that the arms can be passed over the flexible line laterally of the flexible line; and
   means in the base for engaging arms of a similar said clip remote from a base of said similar clip, whereby a plurality of said clips can be chained sequentially to position the flexible lines in a stable orderly array.

15. The clip as defined in claim 14, wherein the pocket has an internal dimension substantially equal to an outer dimension of the flexible line, the internal dimension of the pocket being larger than a spacing between the arms.

16. The clip as defined in claim 14, wherein the clip is distinctly identifiable over said similar clip by at least one of color, size, shape and labelling.

17. The clip as defined in claim 14, wherein the pocket is dimensioned to engage an intravenous line.

18. The clip as defined in claim 14, wherein the clip is an integral plastic body.

19. A clip for organizing flexible lines such as hospital tubing, comprising:
   a base;
   a pair of coextensive resilient arms connected to the base and protruding from the base;
   at least one pocket in the clip, dimensioned to receive and engage one of the flexible lines, the pocket being defined by a hole through the clip bounded at least partly by at least one of the base and at least one of the arms, the pocket opening between the arms such that the arms can be passed over the flexible line laterally of the flexible lines;
   means in the base for engaging arms of a similar said clip remote from a base of said similar clip whereby a plurality of said clips can be chained sequentially to position the elongated bodies in a stable orderly array; and,
   at least one protrusion on at least one of said base and said arms, the protrusion of said at least one of said base and said arms engaging in a corresponding engagement hole in an other of said base and said arms.

20. The clip as defined in claim 19, wherein the arms are spaced and the protrusion extends to connect the base and the arms when the arms are at rest, the arms being resiliently movable such that the protrusion can disengage, the protrusion snapping resiliently into the engagement hole when aligned therewith.

21. The clip as defined in claim 20, wherein the base has a cavity for receiving the arms of said similar clip and comprising protrusions on the arms of said similar clip facing outwardly to snap into corresponding engagement holes in the base.

22. A method for organizing resilient lines in an array, comprising the steps of:
   selecting a clip for designating a line to be installed in the array, the clip having means for engaging the line and means for engaging a similar said clip such that the clips are positioned sequentially in line;
   affixing the clip to the line near a point along the line at which the line can be brought adjacent another line to be included in the array; and,
   affixing an additional said clip to said another line and attaching the clip and the additional clip, whereby the clip and the additional clip, as affixed, maintain relative positions of the line and said another line.

23. The method of claim 22, wherein the clip and the additional clip are distinguishable by at least one of size, shape, color and labelling, and further comprising attaching corresponding distinguishable clips to the resilient lines at a point remote from the initial point, whereby individual said resilient lines are readily identifiable at said initial point and said point remote from the initial point, and the resilient lines are positioned in an orderly manner.

24. The method of claim 22, wherein said clip and said additional clip are affixed to their respective lines adjacent one of a source and a destination in a predetermined array, and at least at one additional place along a length of said respective lines.

25. The method of claim 24, further comprising affixing at least one further said clip and further said additional clip to said respective lines at a point remote from said predetermined array, in at least one further array corresponding to said predetermined array in at least one of position, color, size, and shape of the clips.

* * * * *